United States Patent [19]

Davidson et al.

[11] Patent Number: 5,116,551

[45] Date of Patent: May 26, 1992

[54] METHOD AND APPARATUS FOR PRODUCING AN ARTICLE BY MICROWAVE HEATING

[76] Inventors: Roderick I. Davidson, Marbaix House, Bessemer Road, Basingstoke RG21 3NT; Peter R. Hornsby, 31 Manor Way, Chesham, Buckinghamshire HP5 3BH, both of England

[21] Appl. No.: 698,373

[22] Filed: May 9, 1991

Related U.S. Application Data

[63] Continuation of Ser. No. 435,456, filed as PCT/GB88/00347, May 4, 1988, abandoned.

[51] Int. Cl.$^5$ .................... B29C 41/14; B29C 41/42; B29C 41/52; B29C 35/08
[52] U.S. Cl. .................... 264/26; 264/40.2; 264/297.8; 264/304; 264/335; 264/337; 264/DIG. 30; 264/DIG. 60; 425/174.8 E; 425/271; 425/274; 425/275; 425/141; 425/437
[58] Field of Search ........ 264/22, 25, 26, 86, 264/87, 301–308, DIG. 60, DIG. 45, 334, 335, 40.2, 215, 216, 337, 297.8, DIG. 30; 425/269, 274, 275, 174, 174.8 E, 174.8 R, 271, 437, 141; 427/45.1, 46

[56] References Cited

U.S. PATENT DOCUMENTS

| | | | |
|---|---|---|---|
| 2,482,418 | 9/1949 | Jenkins | 264/26 |
| 2,492,000 | 12/1949 | Morris et al. | 264/DIG. 45 |
| 3,402,239 | 9/1968 | Brubaker | 264/22 |
| 3,737,488 | 6/1973 | Porter et al. | 264/26 |
| 4,018,962 | 4/1977 | Pedlow | 106/18.18 |
| 4,080,561 | 3/1978 | Thompson | 324/54 |
| 4,083,901 | 4/1978 | Schonfeld | 264/25 |
| 4,304,744 | 12/1981 | Stroud | 264/25 |
| 4,499,036 | 2/1985 | Hawkes, Jr. | 264/26 |
| 4,544,339 | 10/1985 | Itoh | 425/174.8 R |
| 4,675,139 | 6/1987 | Kehe et al. | 264/26 |
| 4,705,658 | 11/1987 | Lukas | 264/25 |

FOREIGN PATENT DOCUMENTS

| | | | |
|---|---|---|---|
| 233846 | 8/1987 | European Pat. Off. | 425/174 |
| 2535119 | 2/1976 | Fed. Rep. of Germany | 264/25 |
| 3149265 | 6/1983 | Fed. Rep. of Germany | 264/25 |
| 2555497 | 5/1985 | France | 264/334 |
| 50-40149 | 12/1975 | Japan | 264/306 |
| 56-121729 | 9/1981 | Japan | 264/25 |
| 57-23851 | 2/1982 | Japan . | |
| 58-24430 | 2/1983 | Japan | 264/25 |
| 58-111749 | 7/1983 | Japan . | |
| 61-121915 | 6/1986 | Japan . | |
| 62-121019 | 6/1987 | Japan | 264/301 |
| 2034629 | 6/1980 | United Kingdom | 264/301 |

*Primary Examiner*—Jeffery Thurlow
*Assistant Examiner*—Mathieu Vargot
*Attorney, Agent, or Firm*—Palmatier & Sjoquist

[57] ABSTRACT

A method and apparatus for producing an article, by covering at least a portion of a microwave heatable former with a liquid-containing material, applying microwave radiation to heat the former so as to leave a dry solid coating on the former, and effecting relative separation between the former and the dry solid coating so as to produce the article.

13 Claims, 1 Drawing Sheet

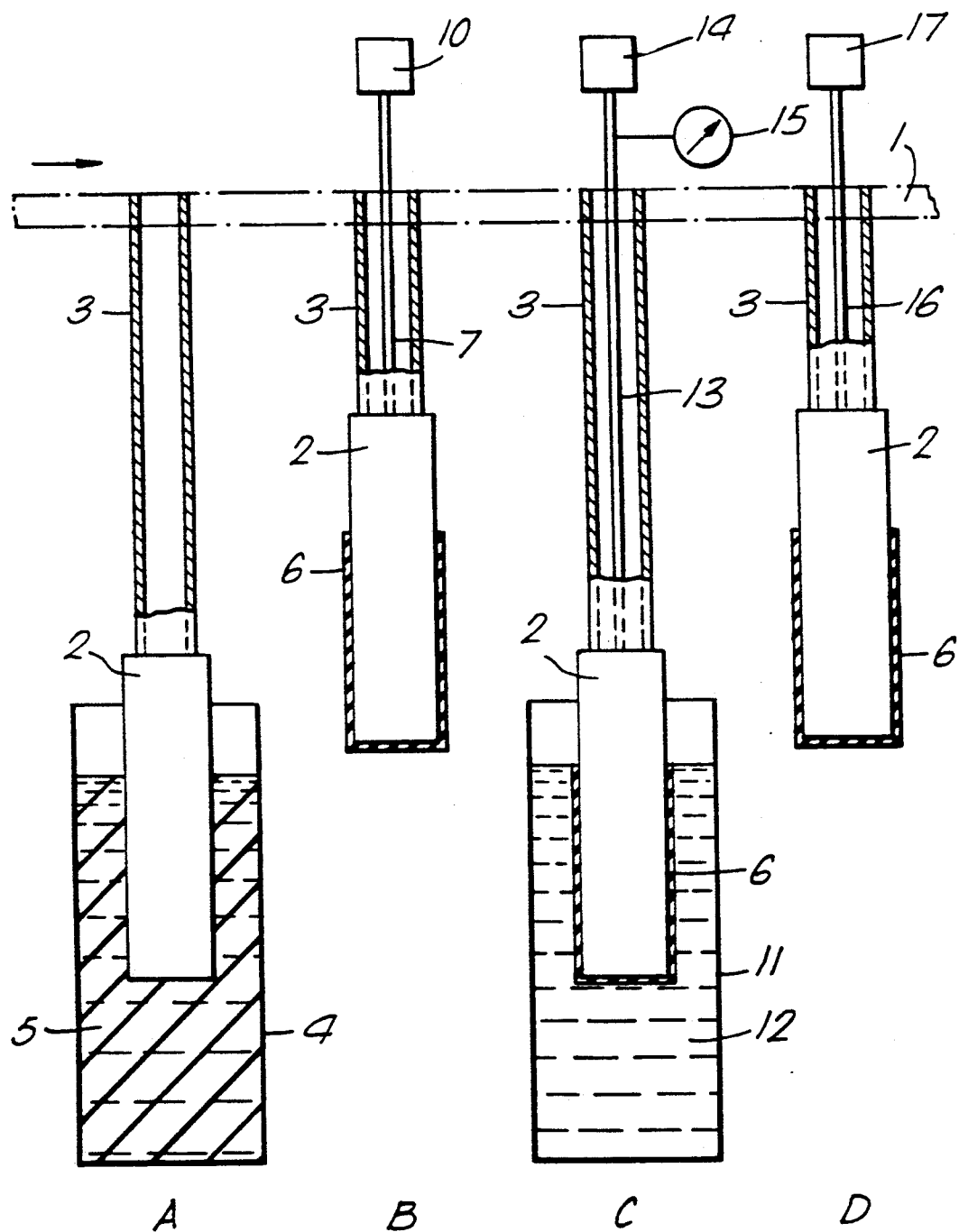

METHOD AND APPARATUS FOR PRODUCING AN ARTICLE BY MICROWAVE HEATING

This application is a continuation of Ser. No. 435,456, filed as PCT/GB88/00347, May 4, 1988, now abandoned.

This invention concerns a method and apparatus for producing an article, such, for example, as a condom or a rubber glove, by microwave heating.

In GB-A-1,310,697 there is disclosed a process for producing a pharmaceutical capsule shell in which a former having an electrically conductive outer surface is dipped into an aqueous thermal gelling coating solution so as to coat it therewith, induction heating of the former is effected so as to gel the coating, and the gelled coating is then dried in a warm air oven. Such a process therefore requires a two-stage heating procedure and does not lend itself to automation since a separate induction heating coil would appear to be required for each former used.

The present invention provides a method of producing an article comprising the steps of:
i) covering an external surface of at least a portion of a former with liquid-containing material;
ii) providing heating so as to leave a dry solid coating on said former; and
iii) effective relative separation between the former and the dry solid coating so as to produce the article;
characterised in that the former is a microwave-heatable former which is heated by being subjected to microwave radiation so as to produce the said dry solid coating.

In the case of the present invention in contrast to the prior art referred to above, only one heating step is required, and this heating step can be readily controlled by varying the power input. When the liquid-containing material contains water (as in a rubber latex) or is a microwave receptive material (e.g. a PVC plastisol), the microwave energy simultaneously heats up both the former and the coating thereon of the liquid-containing material, so effecting drying and/or accelerating gelation.

In the case of the present invention, moreover, automation can easily be achieved since a large number of formers can be heated together within a common multi-mode microwave oven.

The liquid-containing material may be in the form of a solution, suspension or slurry.

The former is preferably made at least predominantly of ceramic material such, for example, as glass or silicon carbide.

The liquid-containing material, moreover, may itself be microwave-heatable.

As indicated above, the liquid-containing material may be a curable or gellable material, e.g. a latex solution or a plastisol.

The microwave radiation may be first employed to raise the liquid-containing material to a temperature at which the material becomes substantially solid, the microwave radiation being thereafter employed to raise the substantially solid material to a higher temperature at which it will be cured or gelled.

The article may be a hollow article. For example, the hollow article may be made of insulating material, the former being electrically conductive; the hollow article, while still on the former, being tested for pinholes therein by maintaining the solid coating on the former in contact with a body of electrically conductive liquid which is at a different potential from that of the former, and noting any factor related to a change in the potential difference between the potential of the former and that of the body of liquid.

The testing may be carried out by introducing the former, with the solid coating thereon, into an earthed tank containing water, and applying a voltage to the former.

The former may be porous, in which case, after the solid coating has been formed on the porous former, a gas may be passed through the latter so as to assist in removing the solid coating therefrom.

The invention also comprises apparatus comprising:
i) a former;
ii) means for covering an external surface of at least a portion of the former with liquid-containing material;
iii) heating means for removing liquid from said material and so as to leave a dry solid coating on said former; and
iv) means for effecting relative separation between the former and the dry solid coating so as to produce the article;
characterised in that the former is a microwave-heatable former and the heating means are arranged to heat the former by subjecting it to microwave radiation so as to produce the said dry solid coating.

The invention is illustrated, merely by way of example, in the accompanying diagrammatic drawing which illustrates the production of a condom by the method and apparatus of the present invention.

Referring to the drawing, an endless, horizontally disposed, support chain 1 supports a plurality of equally spaced apart formers 2 each of which is supported from the chain 1 by a hollow tubular member 3 which is arranged to be raised and lowered (by means not shown). The chain 1 is movable by a motor (not shown) so that each of the formers 2 is moved successively from a latex investment station A to a microwave heating station B to a pinhole testing station C and to a separation station D.

Each of the formers 2 is a porous, electrically conductive microwave-heatable member which is preferably made predominantly of a ceramic material such as silicon carbide or glass. Excellent results can be produced by the use of SILMOR silicon carbide. (SILMOR is a trade mark of Morganite Special Carbons Limited). SILMOR silicon carbide material is produced by the conversion of a mass of porous carbon or graphite to $\beta$-silicon carbide by reaction of the mass with silicon monoxide vapour whereby the surface carbon of said mass reacts with the silicon monoxide vapour to form silicon carbide in situ. This material, has high thermal conductivity and thermal shock resistance allowing rapid heating and cooling without hot-spots developing and has desirable surface finish and other characteristics. The material has the following specification:

| | |
| --- | --- |
| Bulk Density | 2230 kg m$^{-3}$ |
| Conversion depth | Up to 5 mm |
| Hardness | 12+ (Moh's scale) |
| Temperature limit of operation | 1600° C. |
| Thermal expansion | 3.8–4.6 × 10$^{-6}$ °C.$^{-1}$ (25–1000° C.) |
| Bend Strength | 89 MN m$^{-2}$ |
| Young's Modulus | 106 GN m$^{-2}$ |

| | |
|---|---|
| Thermal conductivity | 100 W m$^{-1}$ K$^{-1}$ |

An alternative is to use cast reconstituted silicon carbide to make the formers. Further alternatives are to use sintered β-silicon carbide, which has an excellent rate of heating; or microwave receptive glass or slip-castable ceramics uniformly doped with microwave receptive additives, such as silicon carbide or tin oxide.

At the latex investment station A, each former 2 is lowered into a tank 4 containing rubber latex solution 5 so as to receive a latex investment 6. Alternatively, and depending upon the article being produced, the tank 4 may contain a PVC plastisol (i.e. a suspension of PVC particles in a plasticizer) with or without inclusion of microwave-receptive additives, such as carbon black, aluminium silicate, a metal oxide such as Fe$_3$O$_4$ or a polar liquid additive such as ethylene glycol. Such additives may be used to enhance the heating rate when the former 2 is subjected to microwave radiation at the microwave heating station B.

At the microwave heating station B, the former 2 is subjected, by way of a waveguide 7 introduced through the respective hollow tubular member 3, to microwave radiation generated by a microwave radiation generator 10. The temperature of the rubber latex of the latex investment 6 is first raised rapidly to about 95° C. to remove the water and then, after a predetermined time period, is raised to 130° C. to effect full cure of the rubber. If a plastisol is used in the tank 4, the microwave heating similarly effects gelling of the plastisol. In either case, the microwave energy employed is particularly effective in removing the water since the latter is receptive to microwave energy and therefore rapidly reaches its boiling point and evaporates.

At the pinhole testing station C, the former 2, with the now solid latex investment 6 thereon, is lowered into an earthed tank 11 containing water 12. The former 2 is connected by a conductor 13 to a stabilised voltage source 14, the voltage applied to the former 2 being indicated on a meter 15. If there is a hole through the latex investment 6, the voltage will be lower than would otherwise be the case, and the reading provided by the meter 15 will therefore provide an indication as to whether such a pinhole exists. Although for illustrative purposes a meter 15 is shown in the drawing, electronic equipment (not shown) may be employed to provide an alarm and to stop the process.

At the separation station D, the porous former 2 is connected by a pipe 16, which is introduced through the tubular member 3, to a source 17 of compressed air so that the latter can pass to the interface between the former 2 and the now fully formed condom 6 to render easier the separation of the latter (by means not shown) from the former 2. As will be appreciated, if compressed air is used in this way, it is important to ensure that the latex does not become keyed in the pores of the former so as to block the pores. This may be effected by control of pore size and/or the use of a non-toxic release agent on the surface of the former prior to its investment with the latex.

The use of microwave-heatable formers 2 in the method described above permits a reduction in the cycle time since the formers 2 can be heated and cooled much more rapidly than those heated by other methods. Since, moreover, the formers 2 are electrically conductive, it is not necessary to remove the finished condoms from them and mount them on separate supports in order to test them.

The use of a porous former, in addition to rendering it possible to use the method described in the preceding paragraph, also allows the possibility of increased cooling rates after the former has passed through the microwave heating station B. Additionally, the use of a porous former to produce a hollow product enables the latter to be tested for pinholes by inflating it under internal air pressure whilst it is still attached to the former. Such a procedure could be used in substitution for the testing method described above. However, it will of course be appreciated that the formers 2 are not necessarily porous.

The method illustrated in the drawing is also suitable for the production of other hollow articles, such as rubber gloves. However, the articles which can be produced by the method of the present invention are not necessarily hollow since sheet articles such as thick section plasticised PVC components may also be produced thereby. Furthermore, the method can be used to produce foamed plasticised PVC or expanded rubber parts, using air entrainment methods (frothing) or chemical blowing agents to yield a porous internal structure.

When the liquid-containing material used in the present invention is a rubber latex solution, the heating effected by the former causes water vapour to be released from the rubber article, on heating and curing which tends to diffuse away from the internal surface of the rubber article (i.e. at the surface of the former), thus reducing the tendency to form blisters or defects from entrapped water vapour, as is sometimes the case with existing technology.

The method of the present invention can also be used in the curing of thermosetting plastics compositions. In many cases, such as epoxy and polyester resins, this involves polymerisation of a monomer or prepolymer to a high molecular weight infusible network structure using catalysts, accelerators, and frequently applied heat. Alternatively as in the thermal vulcanisation of rubbers, the method may involve cross-linking of a previously formed high polymer with unsaturated bonds along the polymer chain, which provide sites for further reaction and chemical bonding between chains.

Thermosetting polymers of the type mentioned above, may contain a wide variety of additives to modify their properties such as glass or carbon fibres to enhance stiffness and strength and/or fillers, which for example, in rubber compositions increase hardness and wear resistance.

The cure times during the processing of thermosetting compositions are accelerated by the method of the present invention, particularly if the polymer or precursor resin is itself microwave-responsive (as is the case for polyester and epoxy resins) or microwave receptive additives (such as carbon black in rubber compositions) are included. Furthermore, by this means, a resin can cure more uniformly, since it is not solely dependent on conducted heat from the surface of the former but also heats up internally. This in turn can result in improved physical properties (e.g. strength) of the composite.

It is desirable that the former should have the following properties:

It should be sufficiently transparent to microwave energy to allow penetration and heating of the curable composition.

It should have sufficient temperature resistance to withstand long-term heating at, and/or repeated heating to, the temperatures required to cure the resin (typically up to 200° C.).

It should be chemically resistant to the chemicals in contact with its surface, and possible reaction by-products.

It should be rigid, durable and distortion free under heating temperatures.

It should be wear resistant, particularly in a curing operation in which the thermoset formulation continuously moves across the surface of the former.

Ideally, when placed in a microve field, it should heat up uniformly, without hot spots. (This situation is clearly aided in ceramics having a high thermal conductivity).

We claim:

1. A method of producing an article comprising the steps of:
   a) coating an external surface of at least a portion of a microwave-heatable, ceramic former with liquid-containing material;
   b) subjecting said former to microwave radiation sufficiently so as to heat said former and remove liquid from the liquid-containing material to thereby leave a dry solid coating on said former; and
   c) effecting relative separation between the former and the dry solid coating so as to produce the article.

2. A method as claimed in claim 1, wherein the former is made at least predominantly of microwave receptive glass or silicon carbide.

3. A method as claimed in claim 1, wherein the liquid-containing material is microwave-heatable so as to heat when exposed to microwave radiation both internally and through conduction from the former.

4. A method as claimed in claim 3, wherein the liquid-containing material is a curable or gellable material.

5. A method as claimed in claim 4, further comprising that the liquid-containing material is a latex solution or a plastisol.

6. A method as claimed in claim 4, further comprising that the microwave radiation is first employed to raise the liquid-containing material to a temperature at which the material becomes substantially solid, the microwave radiation being thereafter employed to raise the substantially solid material to a higher temperature at which it will be cured or gelled.

7. A method as claimed in claim 1, wherein the article is a hollow article.

8. A method as claimed in claim 7, wherein the hollow article is made of insulating material, the former being electrically conductive; further comprising testing the hollow article on the former for pinholes by the steps of maintaining the solid coating on the former in contact with a body of electrically conductive liquid which is at a different potential from that of the former, and noting any factor related to a change in the potential difference between the potential of the former and that of the body of liquid.

9. A method as claimed in claim 8, wherein the testing is carried out by introducing the former with the solid coating thereon, into an earthed tank containing water, and applying a voltage to the former.

10. A method as claimed in claim 7, wherein the hollow article is a glove or condom.

11. A method as claimed in claim 1, wherein the former is porous.

12. A method as claimed in claim 11, further comprising after the solid coating has been formed on the porous former, passing a gas through the latter so as to assist in removing the solid coating therefrom.

13. Apparatus for producing an article comprising a ceramic, microwave-heatable former; means for coating an external surface of at least a portion of the former with liquid-containing material; means for subjecting the former to microwave radiation to heat said former and thereby heating and removing liquid from said material so as to leave a dry solid coating on said former; and means for effecting relative separation between the former and the dry solid coating so as to produce the article.

* * * * *